United States Patent [19]

Schittenhelm

[11] 4,124,799

[45] Nov. 7, 1978

[54] ARRANGEMENT FOR EXAMINING A BODY WITH IONIZING RADIATION

[75] Inventor: Rudolf Schittenhelm, Erlangen, Germany

[73] Assignee: Siemens Aktiengesellschaft, Berlin & Munich, Germany

[21] Appl. No.: 772,318

[22] Filed: Feb. 25, 1977

[30] Foreign Application Priority Data

Mar. 5, 1976 [DE] Fed. Rep. of Germany ....... 2609226

[51] Int. Cl.$^2$ ..................... A61B 6/00; G01D 18/00; G01N 23/08
[52] U.S. Cl. ................................. 250/252; 250/445 T
[58] Field of Search .................... 250/252, 445 T, 360

[56] References Cited

U.S. PATENT DOCUMENTS

| 3,778,614 | 12/1973 | Hounsfield | 250/445 T |
| 3,881,110 | 4/1975 | Hounsfield et al. | 250/360 |
| 4,053,780 | 10/1977 | Sparks | 250/445 T |

FOREIGN PATENT DOCUMENTS

| 402,070 | 4/1974 | U.S.S.R. | 250/252 |
| 425,146 | 9/1974 | U.S.S.R. | 250/252 |

*Primary Examiner*—Alfred E. Smith
*Assistant Examiner*—T. N. Grigsby
*Attorney, Agent, or Firm*—Hill, Gross, Simpson, Van Santen, Steadman, Chiara & Simpson

[57] ABSTRACT

In radiotherapy, for example, a computer-tomogram is to be formed with a conventional relatively low dosage but with sufficient information content to enable the working out of an irradiation plan with a specific selected isodose distribution. Since the normally measured attenuation coefficients are not valid with respect to substantially harder x-radiation or gamma radiation, the present disclosure teaches the introduction of test bodies into the spacial region to be scanned in generating the computer tomograph, such test bodies having the same percentage contents of the same elements as are present in the particular body volume to be examined and having a density which is adapted as far as possible to such body volume, the density however being graduated such that graduated attenuation coefficients are recorded for the test bodies in the resultant computer tomogram. Thus it is possible to find a test body section whose attenuation coefficient is identical with that of the body tissue to be subsequently subjected to radiation therapy. Since this test body section also quantitatively manifests the same elements, the attenuation coefficient of the test body agrees with that of the body tissue to be treated even in the case of radiation energies and types of radiation used in radiotherapy. Thus, by examining the attenuation coefficients of the corresponding section of the test body with the particular type of radiation to be used for radiotherapy, the matrix of attenuation coefficients contained in the computer tomogram may be transcribed into a matrix for the type of radiation to be used for the radiation therapy. This applies not only to x-radiation or gamma radiation, but also any random type of ionizing radiation, such as, for example, electron, proton and neutron radiation. As a further development, two identical test bodies may be arranged on opposite sides of the body during scanning so that the difference between the attenuation coefficients associated with these two test bodies is a measure of the hardening of the x-radiation on passage through the body of the patient. This information enables a refinement in the precision of the remaining attenuation coefficients of the computer tomograph. As a specific example, each test body may contain several hermetically sealed samples of the body substance to be examined, the samples having a known but graduated density.

8 Claims, 4 Drawing Figures

ARRANGEMENT FOR EXAMINING A BODY WITH IONIZING RADIATION

BACKGROUND OF THE INVENTION

The invention relates to an arrangement for examining a body with ionizing radiation, comprising means for scanning a spacial region into which the body region to be examined can be brought, from numerous angular positions with a beam having a pencil-like to a fan-like formation, with radiation detectors arranged on the opposite side of the spacial region in a centered or aligned fashion so as to receive the transmitted beam. As is well known in the art, a computer may be provided for processing the output signals from the detectors, so that the output signals may be stored in the form of digitally coded numerical information from which a matrix of measured attenuation coefficients may be obtained.

In recent years, arrangements of this type have become known as so-called computer tomographs. The radiation source used is an x-ray tube which is operated at a constant dose rate. Usually the radiation is collimated into a thin pencil-shaped beam. This beam is scanned over the body region to be examined along the layer plane by means of parallel movement or displacement of the x-ray tube together with the radiation detector. The radiation detector measures the dose rate of the x-ray beam which is transmitted through the body under examination. Since the dose rate of the non-attenuated beam is known, the attenuation of the dose rate can be determined from the two values. When the penetration density is known, the attenuation coefficient of the particular segmental region penetrated by the rays can be calculated. The spacial region is penetrated by the rays from a large plurality of directions. From the measured values obtained in this way, it is possible to calculate and print out or record a distribution of the attenuation coefficients for the respective spacial elements, that is, a matrix of attenuation coefficients, by way of an approximate calculation carried out in a computer. A matrix of attenuation coefficients of this type, that is a computer tomogram, may be displayed, for example, in gray tones or color gradations on the fluorescent screen of a television display unit. As so displayed, the computer tomogram shows not only the external contours of the body to be examined, but also the contours of the tissues or organs contained therein in gradations of their absorption coefficients. An image display such as this can be diagnostically evaluated in the same way as a transverse layer photograph.

In radiotherapy, a computer tomogram of this type is just as helpful for drawing up an irradiation plan as a conventional transverse layer photograph. However, the information content of a computer tomogram of this type is not sufficient for working out an irradiation plan with a specific selected isodose distribution.

1. The measured attenuation coefficients apply solely to the energy of the x-radiation which is used to generate the computer tomograph. However, much harder x-radiation or even gamma radiation from radioisotopes is used in radiation therapy. Therefore, the measured attenuation coefficients are not valid for this hard, penetrating radiation. Nor can they be readily converted, because the attenuation coefficient is dependent in a complex manner upon the density of the tissue, the energy of the x-radiation, and the atomic number of the elements contained in the individual tissue section, and at least two of these variables are unknown.

2. The attenuation coefficients measured in the computer tomograph are already invalidated in the region of the body to be examined as a consequence of the inevitable hardening of the ray spectrum as the rays penetrate the body. This invalidation of the attenuation coefficients is indeed usually corrected by an estimated correction factor which can be fed into the computer. The inaccuracies in the absolute attenuation coefficients connected with the estimation scarcely interfere in diagnostic evaluation. However, they would be obstructive in the drawing up of an irradiation plan. For all these reasons, it has repeatedly been necessary in the past to resort to elaborate experiments in order to determine a reasonably coordinated irradiation plan. The work involved increases exponentially with the improvement in the quality of the irradiation plan which is to be attained.

SUMMARY OF THE INVENTION

The object of the present invention is to point out a way whereby it is possible, on the basis of a computer tomogram recorded via conventional scanning equipment of the diagnostic type, to obtain the additional information which permits the precise determination of the attenuation coefficients for any type of radiation and which is therefore absolutely essential for working out an irradiation plan.

Accordingly, in an arrangement of the type intially described, test bodies with the same percentage contents of the same elements as are present in the particular body volume to be determined and with a density adapted as far as possible to the body volume, but graduated, are introduced in accordance with the invention into the spacial region to be scanned by the beam. What is achieved thereby is that attenuation coefficients are also recorded for the test bodies in the computer tomogram so that attenuation coefficients obtained for the test bodies may be compared with the attenuation coefficients of the corresponding body sections to be examined. This comparison is possible here for the first time, because these test bodies exhibit the same percentage contents of the individual chemical elements as the body region to be examined. They therefore also exhibit the same attenuation coefficients for the same radiation hardness, insofar as they also correspond in regard to density. By subdividing the test bodies into sections with graduated densities all of which are simultaneously included in the scanning process, it is always possible, given a sufficiently fine subdivision, to find a test body section whose attenuation coefficient is identical with that of the body tissue to be examined. Since this test body section also quantitatively manifests the same elements, the attenuation coefficient of the test body agrees with that of the body tissue to be examined even in the case of radiation energies and types of radiation used in radiotherapy. If one such test body with graduated densities is used for each of the body substances occuring, such as, for example, bone tissue, fatty tissue, lung tissue, muscle tissue, etc., and if the attenuation coefficients of the corresponding sections of these test bodies are examined with the particular type of radiation selected for radiotherapy, the matrix of attenuation coefficients contained in the computer tomogram for the type of radiation used in diagnostic computer tomograph examination may be transcribed into a matrix for the type of radiation to be used for radiation therapy by theoretically or experimentally determining the attenuation coefficients of the test substances in relation to the therapy radiation. The latter may be used as the basis for the exact calculation of irradiation plans. This applies not only to x-radiation or gamma radiation, but also any other type of ionizing radiation, such as, for example, electron, proton and neutron radiation.

In another particularly advantageous embodiment of the invention, two identical test bodies may be arranged in the region scanned by the beam, for example on opposite sides of the body to be examined. The difference between the attenuation coefficients associated with these two test bodies, which are identical with one another, is a measure of the hardening of the x-radiation spectrum on passage through the body of the patient. The attenuation coefficients recorded during the passage of the beam through the body are to be corrected in the same ratio in order to obtain attenuation coefficients over the entire radiation path which are based on one and the same ray quality and thus are compatable with one another. This represents an improvement with regard to the method using estimated correction factors which has been practiced up to the present time. In this manner, more precise attenuation coefficients are obtained.

In an expedient embodiment of the invention, the test body may contain several hermetically sealed samples of the body substance to be examined, the samples having a known but graduated density. This ensures in the simplest possible way that the same distribution of chemical elements is present as in the body tissue to be examined. It hardly makes any difference if these test bodies are made more stable by heating.

In a further development of the invention, more precise measurement results are obtained if, in instances where bone substances are used, these bone substances are assigned to a specific age group per test body. It has been found that certain minerals accumulate in the bones of healthy humans in the course of aging. It is only by utilizing test bodies containing a bone substance which corresponds to the same known age group to which the patient to be examined belongs that exact results are obtained.

In another advantageous embodiment of the invention, the test body may consist of a homogeneous synthetic plastic material which contains all of the elements occurring in the particular body substance to be determined in corresponding percentage proportions, but which is graduated in sections as to density. This does indeed initially require a thorough analysis of the most diverse body substances in a precise determination of the quantitative proportions of the diverse elements. However, synthetic or plastic test bodies such as these are capable of lasting indefinitely and they are easier to handle.

In an advantageous further embodiment of the invention, the test bodies may be placed in the spatial region to be scanned directly on the body to be examined. This provides not only the advantage that the attenuation coefficient of air is eliminated upon comparison of the attenuation coefficients of the test bodies and of the body to be examined, but also provides the additional advantage that the influence or effect of hardening of the radiation spectrum can be kept at a minimum during the examination of the body regions in proximity of the surface.

Other objects, features and advantages of the invention will be apparent from the following detailed description taken in connection with the accompanying sheet of drawings.

DETAILED DESCRIPTION

Figure 1:
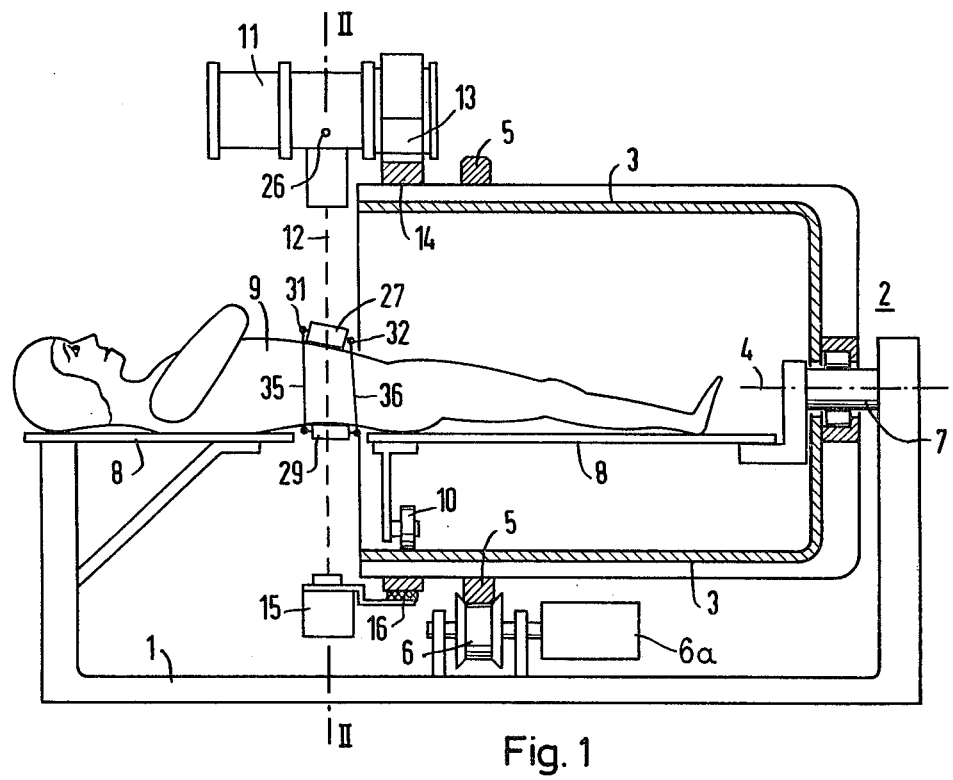
FIG. 1 is a somewhat diagrammatic longitudinal sectional view of a computer tomograph apparatus and illustrating the test bodies of the present invention in association with a patient during a scanning operation.

In FIG. 1 reference numeral 1 designates the support stand of a computer tomograph apparatus 2. A cylinder 3 open at one end is rotatably mounted on the stand 1 for rotation about a horizontal axis 4 coinciding with its axis of symmetry. At its open end, the clyinder 3 is surrounded by a barrel ring 5 which is supported by a plurality of rollers such as the roller 6 illustrated in FIG. 1 which can be rotated by means of a motor diagramatically indicated at 6a for the purpose of rotatably driving the cylinder 3. At its closed end, the cylinder 3 is guided on a horizontal axle stub 7 of support stand 1. Parallel to the axis of symmetry of the cylinder 3 and approximately ten centimeters (10 cm) below it, a patient supporting plate or table 8 is mounted within the interior of the cylinder 3. A patient 9 is illustrated lying on the patient supporting table 8. Inside the cylinder 3, the patient supporting table is fixedly suspended by means of the axle stub 7 of the support stand 1, the axle stub 7 being fixedly held against rotation by means of its attachment to the support stand 1 at the exterior side of the cylinder 3. In the plane of the open end of the cylinder 3, the patient supporting table 8 is provided with a gap several centimeters wide. The free end of the inner part of the patient supporting table 8 is supported on the inner diameter of cylinder 3 via a running wheel 10.

Figure 2:
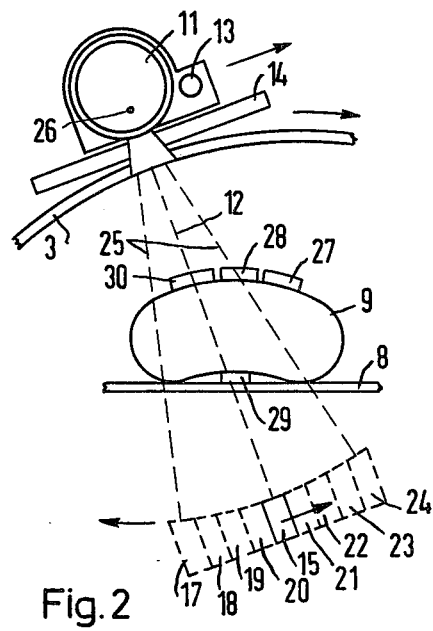
FIG. 2 is a diagrammatic transverse sectional view taken generally along the plane II—II of FIG. 1.

At the open end of the cylinder 3, an x-ray tube 11 is mounted on the circumference or periphery of the cylinder in such a manner that its central ray indicated by the dash line 12 is aligned so as to be directed perpendicularly of the tangent to the circumference of the cylinder as seen in FIG. 2. The x-ray tube 11 can be moved or displaced by means of a motor 13 along a slide rail 14 arranged tangentially on the exterior of the cylinder 3 as shown in FIG. 2. When the x-ray tube is moved or displaced along the slide rail 14, the central ray 12 of the x-ray tube 11 remains parallel to the orientation thereof shown in FIG. 2 and perpendicuar to the axis of the slide rail 14. On the opposite side of horizontal cylinder 3, a radiation detector 15 is arranged so that it is centered or in alignment with the central ray 12 of x-ray tube 11. The radiation detector 15 is coupled with x-ray tube 11 for joint lateral movement such that as x-ray tube 11 is moved or displaced along sliding rail 14, the detector 15 is moved on its own slide rail 16 which is mounted on the cylinder periphery and extends parallel to slide rail 14. Thus, the detector 15 retains its alignment with the central ray 12 of the x-ray tube 11 during the joint lateral shifting of tube 11 and detector 15 along the respective slide rails 14 and 16.

Instead of a single moveable or displaceable radiation detector 15, it is also possible, as illustrated in broken lines in FIG. 2, to fixedly arrange a series of closely adjacent ray detectors such as 17-20, 15, and 21-24 on the cylinder and in the path of lateral dispacement of the central ray 12 as the x-ray tube 11 moves along the slide rail 14 with the detector arrangement 15, 17-24 fixed. In this case, the radiation detectors 15, 17-24, during displacement or movement of the x-ray tube 11 along the slide rail 14, would deliver a measuring signal one after the other as the central ray 12 successively impinges thereon. Finally, it is also possible, instead of using a beam which has been diaphragmed to a pencil-like cross-section, as represented by central ray 12, to use a beam as indicated at 25 in FIG. 2 which is increased or opened out in a fan-like formation in the plane of the spacial region to be scanned, so that all of the radiation detectors 15, 17 through 24, disposed in this plane, receive radiation simultaneously without movement or displacement of the x-ray tube 11 along the slide rail 14. In this instance, the movement or displacement of the x-ray tube 11 along rail 14 may be eliminated. However, the radiation detectors as illustrated in broken lines in FIG. 2 must then be arranged in a semicircular formation about focus 26 of x-ray tube 11, so that the radiation paths from the focus 26 of the x-ray tube to each of the radiation detectors are of equal length. After each scanning of the spacial region to be examined, whether it be by means of moving or displacing x-ray tube 11 along the slide rail 14 with simultanteous movement of a single radiation detector 15, or whether it be by means of a beam 25, which has been opened out in a fan-like formation with respect to the cross sectional plane of cylinder 3, with simultaneous energization of all radiation detectors 15, 17 through 24, arranged in the cross sectional plane, cylinder 3 is further rotated for example approximately one degree (1°) about horizontal axis 4, and the same scanning operation is repeated.

FIGS. 1 and 2 illustrate test bodies 27, 28, 29, 30, which are placed directly on the body of patient 9 in the cross sectional plane to be penetrated by the rays. The test bodies are provided on both sides with eyelets such as indicated at 31, 32, 33, 34 in FIG. 3, and on both sides of the plane to be penetrated by the rays, are fastened to the body of the patient for example by means of rubber cords such as indicated at 35, 36, 37, 38, 39, 40 in FIG. 3, which are inserted into the eyelets. One of the test bodies 29 is fastened to the back of the patient. This test body 29 has precisely the same composition and density gradation as another test body 28 fastened on the opposite side of the patient 9.

Figure 3:
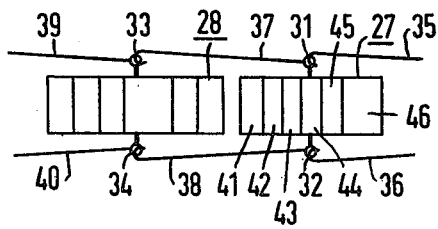
FIG. 3 is a plan view showing two test bodies with graduated density corresponding to two of the test bodies shown in FIG. 2.

FIG. 3 illustrates a plan view of two of these test bodies 27, 28. Each of these test bodies is provided with a substance which manifests the same various chemical elements in precisely the same percentage quantities in homogeneous distribution as the body tissue to be examined during the scanning procedure, whether it be liver tissue, muscle tissue, heart muscle tissue, fatty tissue, bone tissue, etc. However, in the various sections such as indicated at 41 through 46 for the individual test body 27 and for the similarly graduated density sections of the other test bodies 28, 29 and 30, the densities of each substance are graduated relative to one another. For example, if the test body 27 is provided with a substance which manifests the same various chemical elements in precisely the same percentage quantities and in homogeneous distribution so as to correspond to bone tissue, for example, then the section 41 will contain the substance corresponding to such bone tissue but having the least density, for example, while the sections 42, 43, 44 and 45 will have progressively greater density of the same substance and the section 46 will have the greatest density of such substance, the range of density between the minimum density of section 41 and the maximum density of section 46 corresponding to the range of density which may be encountered for the bone tissue of the patient under examination. The number of successive sections 41 through 46 for each of the body tissues to be examined will have a sufficient number of sections so as to provide one section which accurately matches the body tissue of the patient with the desired degree of accuracy. The sections such as 41 through 46 of the test bodies 27-30 may be of variable width, for example, according to a random code system so that the test bodies can be subsequently distinguished from one another in the computer tomogram such as indicated in FIG. 4.

Figure 4:
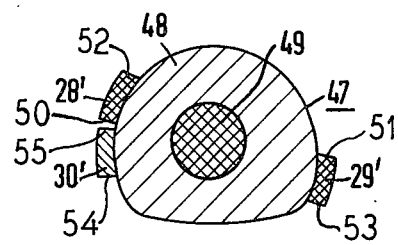
FIG. 4 illustrates a simplified computer tomogram of a thigh with test bodies also being reproduced as part of the tomogram.

FIG. 4 illustrates a greatly simplified computer tomogram 47 of an upper thigh. For purposes of clarity, only muscle substances 48 and bone substances 49 are distinguished from one another in the illustrated computer tomogram. These two types of tissues have been differently shaded corresponding to their different attenuation coefficients. In the computer tomogram of FIG. 4, test bodies 28, 29 and 30 are recognizable as images 28', 29' and 30', the test bodies 28, 29 and 30 having been fastened to the upper thigh of the patient during the scanning operation from which the tomogram of FIG. 4 was produced. In the illustrated example, the composition of the substance within the test bodies 28 and 29 has the same various chemical elements in precisely the same percentage quantities in homogeneous distribution as the bone substance of the body part under examination, each such test body having successive sections corresponding to 41-46 in FIG. 3 with progressively greater density, and the test bodies thus having images 28' and 29' in FIG. 4 which exhibit corresponding sections of progressively greater density. Thus an end section such as indicated at 50 of image 28' and an end section such as indicated at 51 of image 29' may exhibit a minimum density for the bone substance under examination, while the opposite end section such as indicated at 52 and 53 of the images 28' and 29' may exhibit the maximum density with respect to the bone substance under examination. Similarly for the case of muscle tissue, the end section 54 of image 30' may exhibit the minimum density of such muscle tissue while the end section 55 may exhibit the maximum density. Accordingly, the density recorded for the actual muscle substance 48 will be found to conform with one of the density sections in the range between sections 54 and 55, and the density observed for the bone substance 49 under examination will be found to correspond in density to one of the density sections between the end sections 50 and 52 and between the end sections 51 and 53 of the images 28' and 29' of the test bodies 28 and 29.

In operation of the system shown in FIGS. 1 through 3, if an irradiation plan is to be drawn up for a patient, the patient 9 is positioned in the computer tomograph apparatus 2 in such a manner that the region containing the seat of the disease coincides with the spacial region scanned by the x-ray beam of the computer tomograph equipment. Those test bodies 27, 28, 29, 30, which correspond in their composition to the types of tissue assumed to be present in this region are then placed on the patient. The test bodies are placed in such a manner that they are also scanned by the x-ray beam 12, or 25. To this end, rubber cords such as 35-40 are laterally inserted into the eyelets such as 31-34 of the test bodies and are guided around the body of the patient in the manner of a belt. In so doing, caution should be exercised to ensure that these rubber cords are disposed laterally of the spacial region to be scanned by the x-ray beam. The matrix of atenuation coefficients which is represented by the tomogram of FIG. 4 will then contain the attenuation coefficients not only for the body region under examination but also for the test bodies 27-30 placed on the patient. According to the invention, the radiation spectrum utilized in developing the computer tomogram may be the conventional diagnostic spectrum, and the tomogram of FIG. 4 is to be considered as having been obtained in this way. The two corresponding test bodies 28, 29, FIG. 2, which are fastened on opposite sides of the body of the patient 9, permit conclusions to be drawn regarding the degree of hardening of the x-ray beam spectrum which has actually taken place as a result of the passage of the beam through the body. This hardening is not adequately compensated in the result of the measurement if the calculated attenuation coefficients of these two identical test bodies do not correspond with one another. The attenuation coefficients as calculated and corrected to allow for the radiation hardening in the individual space elements of the body to be examined can be assigned to specific organs and types of tissue by virtue of the known anatomy of the body. If the identified attenuation coefficients of these types of tissues are compared with the attenuation coefficients of the test bodies 27-30 assigned to the same types of tissue, it is only that density value from the density gradation of each one of these test bodies which corresponds to the particular density value of the associated type of tissue which also has the same attenuation coefficient. However, since the attenuation coefficients of the test bodies for the particular type of radiation to be selected for therapy are known or can be measured, the matrix of the attenuation coefficients obtained in the computer tomograph can be transcribed into a matrix of the attenuation coefficients for the radiation to be selected. The matrix of attenuation coefficients thus obtained for the therapy radiation makes possible a precise specification of an irradiation plan. This applies to any type and energy of ionizing radiation.

It will be apparent that many further modifications and variations may be effected without departing from the scope of the novel concept and teachings of the present invention.

I claim as my invention:

1. An arrangement for examining a body with ionizing radiation, comprising means for scanning a spacial region into which the body to be examined can be brought, from numerous angular positions with a beam having a pencil-like to fan-like formation, radiation detector means disposed in a centered or aligned fashion on the opposite side of the spacial region for supplying measured attenuation coefficients for the individual radiation paths, thereby to enable the generation of a computer tomograph, characterized in that, in order to determine the density distribution in a matrix of attenuation coefficients, test bodies are introduced into the spacial region to be scanned by the beam, said test bodies having the same percentage contents of the same elements as are present in the particular body volume to be determined, and having a density which is adapted as far as possible to the body volume, said density being, however, graduated.

2. An arrangement according to claim 1, characterized in that two identical test bodies for scanning by the beam are arranged within the spacial region and on opposite sides thereof.

3. An arrangement according to claim 1, characterized in that the test bodies contain a plurality of hermetically sealed samples of the body substance to be investigated with a known graduated density.

4. An arrangement according to claim 1, characterized in that at least one of the test bodies has the same percentage contents of the same elements as are present in the bone substances for a specific age group.

5. An arrangement according to claim 1, characterized in that the test bodies consist of a homogeneous synthetic or plastic material which contains all elements occurring in the particular body substance to be determined in corresponding percentage amounts, but which is graduated in sections as to density.

6. An arrangement according to claim 1, characterized in that the test bodies are placed directly on the body to be examined and within the spacial region to be scanned.

7. An arrangement according to claim 6, characterized in that the test bodies are fastened to the body to be examined in the manner of a belt.

8. An arrangement according to claim 6, characterized in that the test bodies are provided with eyelets at the lateral sides thereof for the purpose of fastening onto the body to be examined.

* * * * *